(12) United States Patent
Tobias et al.

(10) Patent No.: US 9,011,584 B2
(45) Date of Patent: Apr. 21, 2015

(54) END OF SERVICE LIFE INDICATOR FOR RESPIRATOR

(75) Inventors: Peter Tobias, Minneapolis, MN (US); Christopher Scott Larsen, Rockford, MN (US)

(73) Assignee: Honeywell International Inc., Morristown, NJ (US)

( * ) Notice: Subject to any disclaimer, the term of this patent is extended or adjusted under 35 U.S.C. 154(b) by 308 days.

(21) Appl. No.: 13/420,186

(22) Filed: Mar. 14, 2012

(65) Prior Publication Data

US 2013/0047982 A1 Feb. 28, 2013

Related U.S. Application Data

(60) Provisional application No. 61/527,300, filed on Aug. 25, 2011, provisional application No. 61/556,606, filed on Nov. 7, 2011.

(51) Int. Cl.
| | |
|---|---|
| *B01D 46/42* | (2006.01) |
| *A62B 18/08* | (2006.01) |
| *A62B 9/00* | (2006.01) |
| *A62B 23/02* | (2006.01) |
| *A62B 18/00* | (2006.01) |

(Continued)

(52) U.S. Cl.
CPC ............... *A62B 18/088* (2013.01); *A62B 9/006* (2013.01); *A62B 23/02* (2013.01); *A62B 18/006* (2013.01); *B01D 2259/4541* (2013.01); *G01N 2001/2285* (2013.01); *G01N 2001/2288* (2013.01); *B01D 53/30* (2013.01); *Y10S 55/33* (2013.01); *Y10S 55/35* (2013.01)

(58) Field of Classification Search
USPC .................. 55/385.1, 471, 472, 473, DIG. 33, 55/DIG. 34, DIG. 35; 96/127, 140, 417, 96/397, 424; 128/201.23, 202.22, 205.27, 128/206.12, 206.21, 201.25, 205.22; 116/206

See application file for complete search history.

(56) References Cited

U.S. PATENT DOCUMENTS

| | | | | |
|---|---|---|---|---|
| 2,577,606 A | * | 12/1951 | Conley | ............................ 96/134 |
| 4,146,887 A | | 3/1979 | Magnante | |
| 4,154,586 A | | 5/1979 | Jones et al. | |

(Continued)

FOREIGN PATENT DOCUMENTS

| | | |
|---|---|---|
| CA | 2628699 A1 | 10/2009 |
| CA | 2628699 A1 | 10/2009 |

(Continued)

OTHER PUBLICATIONS

"International Application Serial No. PCT/US2012/052287, Invitation to Pay Additional Fees and Partial International Search mailed Sep. 3, 2013", 5 pgs.

(Continued)

*Primary Examiner* — Duane Smith
*Assistant Examiner* — Minh-Chau Pham
(74) *Attorney, Agent, or Firm* — Conley Rose, P.C.; Kristin Jordan Harkins

(57) ABSTRACT

A device includes a cartridge containing a filter material. An insert extends through at least a portion of the filter material. The insert has gas sample path with an opening to provide a sample of air that is representative of the saturation of the filter material. A return path may be included in the insert to return sampled gas to the filter material. A gas mask contains a gas sensor and coupled to the cartridge, which may be replaced when saturated.

19 Claims, 5 Drawing Sheets

(51) Int. Cl.
*G01N 1/22* (2006.01)
*B01D 53/30* (2006.01)

(56) References Cited

U.S. PATENT DOCUMENTS

| | | | |
|---|---|---|---|
| 4,155,358 A | | 5/1979 | McAllister |
| 4,200,092 A * | | 4/1980 | Warncke et al. ......... 128/202.26 |
| 4,365,627 A | | 12/1982 | Wing |
| 4,530,706 A | | 7/1985 | Jones |
| 4,886,058 A * | | 12/1989 | Brostrom et al. ........ 128/206.12 |
| 5,158,077 A * | | 10/1992 | Sundstrom ............... 128/205.27 |
| 5,165,395 A * | | 11/1992 | Ricci ........................ 128/202.22 |
| 5,666,949 A * | | 9/1997 | Debe et al. ............... 128/202.22 |
| 5,776,213 A * | | 7/1998 | Flaherty et al. ................. 55/482 |
| 5,861,053 A * | | 1/1999 | Noritake et al. ................ 96/111 |
| 6,044,842 A * | | 4/2000 | Pereira et al. ............ 128/202.27 |
| 6,375,725 B1 | | 4/2002 | Bernard et al. |
| 6,497,756 B1 | | 12/2002 | Curado et al. |
| 6,979,361 B2 | | 12/2005 | Mihayiov et al. |
| 7,118,608 B2 * | | 10/2006 | Lovell .......................... 55/385.1 |
| 7,442,237 B1 | | 10/2008 | Gardner |
| 7,749,303 B2 | | 7/2010 | Wright |
| 7,927,558 B2 | | 4/2011 | Kirollos et al. |
| 7,992,426 B2 * | | 8/2011 | Fleischer et al. ............. 73/31.06 |
| 8,574,331 B2 * | | 11/2013 | Bangera et al. ............. 55/385.1 |
| 2008/0056946 A1 * | | 3/2008 | Ahmad ........................ 422/68.1 |
| 2008/0119753 A1 * | | 5/2008 | Ricciardelli et al. .......... 600/532 |
| 2010/0294272 A1 | | 11/2010 | Holmquist-Brown et al. |
| 2010/0294274 A1 | | 11/2010 | Poirier et al. |

FOREIGN PATENT DOCUMENTS

| | | |
|---|---|---|
| DE | 3613512 A1 | 10/1987 |
| WO | 9612523 A1 | 5/1996 |
| WO | 2008145988 A1 | 12/2008 |
| WO | WO-2008/145988 A1 | 12/2008 |
| WO | 2009029426 A1 | 3/2009 |
| WO | WO-2009/029426 A1 | 3/2009 |

OTHER PUBLICATIONS

PCT/US2012/052287, Invitation to Pay Additional Fees and Partial International Search Report dated Sep. 3, 2013, 5 pages.

PCT/US2012/052287, International Search Report dated Oct. 28, 2013, 6 pages.

PCT/US2012/052287, Written Opinion of the International Searching Authority dated Oct. 28, 2013, 12 pages.

* cited by examiner

END OF SERVICE LIFE INDICATOR FOR RESPIRATOR

RELATED APPLICATIONS

This application claims priority to U.S. Provisional Application Ser. No. 61/527,300 (entitled END OF SERVICE LIFE INDICATOR FOR RESPIRATOR, filed Aug. 25, 2011) and to U.S. Provisional Application Ser. No. 61/556,606 (entitled END OF SERVICE LIFE INDICATOR FOR RESPIRATOR, filed Nov. 7, 2011) both of which are incorporated herein by reference.

BACKGROUND

Today's respirators have no indicator when a breakthrough of harmful gases occurs in their cartridges. Instead the user has to rely on making conservative estimates from previously gathered data, which leads to disposing of cartridges that have a lot of remaining life and, sometimes, to non-detected breakthroughs of cartridges that expose the user to dangerous gases. We could use an End-of-Service-Life Indicator (ESLI) to forecast the breakthrough of harmful gas. An ESLI should provide reliable and accurate warning before 90% of the useful life of the cartridge (which is the regulatory requirement from NIOSH; the useful life is the time when harmful gases do not exceed the permissible exposure limits at the user).

One way of adding an ESLI is integrating the ESLI system into the cartridge (with absorbent downstream from the sensor); but this increases cartridge costs and complicates the communication with the sensor. Additionally, we would have to have as power supply either a disposable battery in the cartridge (costs!) or complicated wiring in the connector thread from the respirator housing. So far, the multiple attempts to integrate ESLI sensors into the cartridges, are believed to have been commercially unsuccessful.

SUMMARY

A device includes a cartridge containing a filter material. An insert extends through at least a portion of the filter material. The insert has gas sample path with an opening to provide a sample of air that is representative of the saturation of the filter material. A return path may be included in the insert to return sampled gas to the filter material.

A respirator includes an air path to provide air to a user, a gas sample path, a gas sensor coupled to the gas sample path to receive and sense a gas sample, a gas return path coupled to the gas sensor to receive the sensed gas sample, and a coupler to couple the air path, gas sample path, and gas return path to a filter cartridge.

A method includes obtaining a sample of air that has traversed a substantial portion of filter material in a respirator filter cartridge to provide to a gas sensor, returning the sample of air to the filter material downstream of the point in the filter material where the sample was obtained, and filtering the return sample of air to provide the sample to a user to breathe.

DETAILED DESCRIPTION

In the following description, reference is made to the accompanying drawings that form a part hereof, and in which is shown by way of illustration example embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software or a combination of software and human implemented procedures in one embodiment. The software may consist of computer executable instructions stored on computer readable media such as memory or other type of storage devices. Further, such functions correspond to modules, which are software stored on a storage device, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system.

A service life indicator for a respirator cartridge utilizes an insert that provides the ability to provide samples from one or more points in the cartridge that are representative of when purifying media is nearing the end of its ability to adequately filter air.

Figure 1:
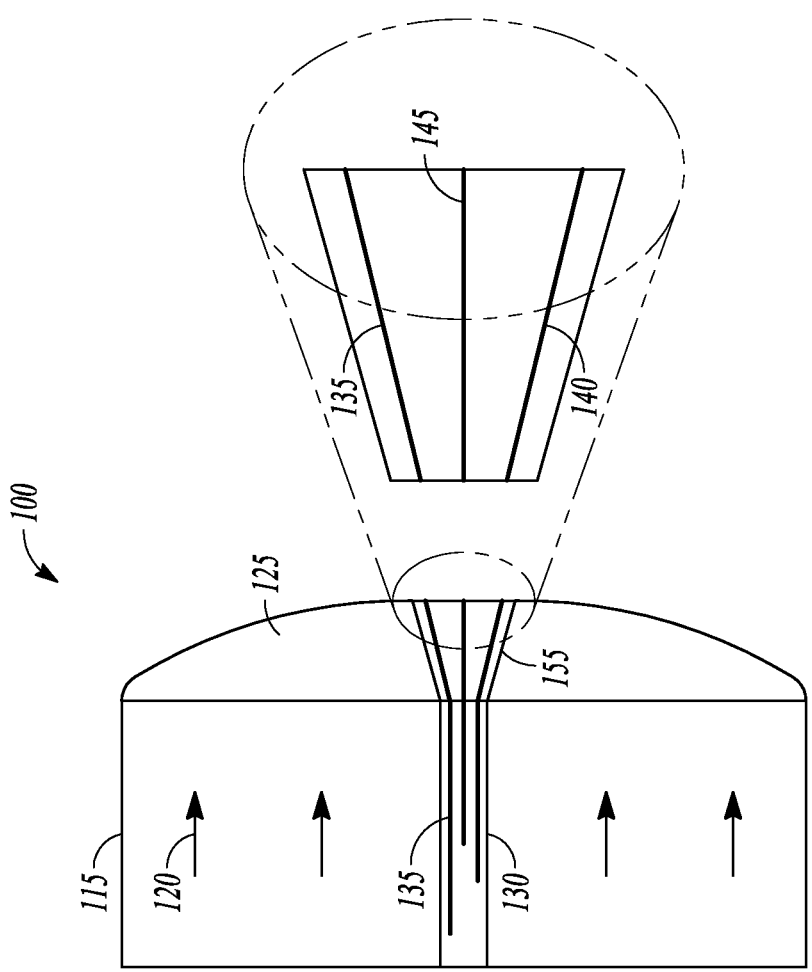
FIG. 1 is a cross section view of a respirator cartridge having an insert with channels, along with an enlarged view of an adapter end of the insert according to an example embodiment.

FIG. 1 is a cross section view of a respirator cartridge 100. The respirator cartridge 100 includes a container 110 having an air purifying element, such as a filter material 115 for filtering air that enters the container and flows in the direction shown by arrows 120. In one embodiment, the container 110 is cylindrical in shape, and has an adapter 125 coupled at one end to connect to a mask or other device for providing filtered air from adapter 125 end of the cartridge 100 to a user. The container may be formed in other shapes in further embodiments, having cross sections including squares, triangles, rectangles, and other polygons.

As the cartridge 100 is used, the filter material 115 may be used to remove gaseous contaminants and/or particulate matter contaminants from air that moves through the filter material 115. The filter material may become saturated beginning at the point of entry of air into the cartridge, and progressing toward the adapter end 125. Particulate matter may include various solid particles, liquid droplets, and/or organic contaminants such as bacteria, viruses, and the like. The particles are generally smaller than about 1 mm, about 100 micrometers, about 10 micrometers, or about 1 micrometer in diameter. Suitable purifying elements may be selected based on the contaminants to be removed from air to be breathed by a user. The filter material may not remove all contaminants, but in some embodiments, the filter material reduces at least one contaminant to acceptable levels.

An insert 130 is positioned within the container 110 extending at least partially through the filter material 115 to the adapter 125, and also extending through the adapter 125 for connection to the mask. In one embodiment, the insert 130 contains at least one channel or path 135 that open to the filter material to receive air that has moved through the filter material. The path 135 extends longitudinally along the insert through the remaining filter material and through the adapter for providing a test sample of air to a sensor. The sensor may be incorporated into the mask to reduce the cost of the cartridge 100, allowing the cartridge 100 to be replaceable when the sensor indicates that the filter material is nearing the end of its useful life. The position of the opening may be selected to be toward the adapter end of the cartridge in one embodiment to ensure that there is still sufficient filter material to continue to filter air for the user for a desired amount of time prior to replacing the cartridge.

In one embodiment, a metal-oxide gas sensor may be used to sense the test sample. In further embodiments, a photo ionization detector or other sensor without significant drift may be used. The sensor may be coupled directly to or within the cartridge 100 or coupled to or within a respirator mask to which the cartridge is adapted to be coupled.

The insert 130 in one embodiment extends all the way through the container 110, and has a consistent cross section throughout its length. This allows the provision of a consistent cross section of filter material throughout the length of the container. Having such a consistent cross section may help ensure that portions of the filter do not allow breakthrough of contaminated air to the user because of some unequal path lengths through the container. The filter saturates from the end of the cartridge where air enters due to user breathing. The consistent cross section helps ensure a saturation front that is fairly smooth. In further embodiments, the insert need only extend to the furthest upstream sampling location.

In one embodiment, the insert 130 contains three paths, 135, 140, and 145. Path 135, as previously described, has an opening within the filter material 115 to collect a gas sample. Path 140 provides a return path for the gas sample after it has been sensed. In one embodiment, the path 140 has an opening downstream from the opening of path 135 within the filter material. When the user breathes in, a difference in pressure is created between the opening of the path 135 and the opening of the path 140, providing force to move the gas sample via path 135 to the sensor and back to the filter material via path 140. In one embodiment, the opening in path 140 returns the sample at a position that enables filter material from the opening to the adapter 125 to filter the sample prior to it reaching the user. The distance between the openings of paths 135 and 140 may be calculated to provide sufficient force to allow the gas to move through the paths at a desired speed.

Path 145 may also be used in some embodiments. It may serve as a return path for either of paths 135 or 140 in various embodiments. In one embodiment, path 135 provides the sample gas, and path 145 provides the return path. In another embodiment, path 140 provides the sample gas, with path 145 providing the return path. The use of two different sets of paths provide the ability to compare the gas sampled at different points to cancel out sensor drift. If sensor sensitivity drift is not cancelled out, the sensitivity may decline over time, reducing the ability to detect when the cartridge is filled.

In some embodiments, the longitudinal distance between the openings of paths 140 and 145 may be the same as that between paths 135 and 140, providing a similar force for transporting gas through the paths. The return path may change depending on the sample point so that the return path is the shortest of the paths involved in obtaining and returning the sample to the filter material. The shortest may be thought of as the path that opens to the filter material closer to the user. Thus, a long path may utilize any shorter path as the return path in some embodiments.

In further embodiments, fans, or pumps may be used, in which case the return path may return sensed air at the same longitudinal point as the same was taken, at any other point within the filter material, or may simply be exited to ambient air.

In one embodiment, the insert 130 widens within the adapter 125 toward the adapter end of the insert at a face 150. This provides separation of the adapter end openings of the paths 135, 140, and 145. The adapter 125 may contain a threaded portion 155 to mate with corresponding threads of a face mask to attach the cartridge to the face mask. Other mechanisms, such as latchable protrusions, or any other mechanism suitable for providing attachment may be used in further embodiments. Filtered air also moves through the adapter to be provided to a user of the face mask. The term face mask is meant to encompass any type of mask that allows connection of cartridges to provide air to a user of the face mask, including helmet type respirators.

Figure 2:
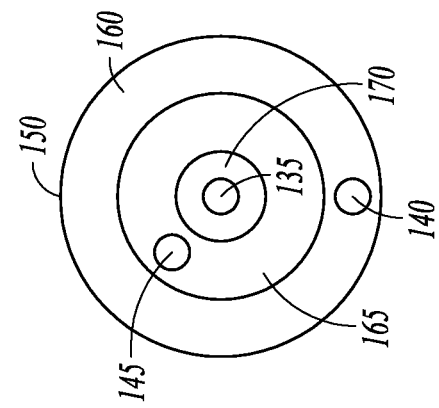
FIG. 2 is a side view of the adapter end of the insert according to an example embodiment.

FIG. 2 is a side view of the adapter end or face 150 of the insert according to an example embodiment. Face 150 is circular in one embodiment, and resembles a bull's-eye. Face 150 contains a separate channel 160, 165, 170 for each of the respective openings of the paths 135, 140, and 145. The channels are concentric, and are separated by rims that are either soft, or contain o-rings to allow a mating connection to corresponding channels in the face mask. The channels thus allow any rotational orientation of an installed cartridge to properly couple the paths to gas paths within the mask that includes the sensor. Thus, the cartridge insert 130 has rotational symmetry. In alternative embodiments, the openings may be simply provided at the face 150 and coupled directly to corresponding openings. In still further embodiments, the insert may continue beyond the face, and have further openings to allow connection to paths in the face mask.

The paths in one embodiment have a constant diameter that is the same as the openings of the paths. The paths are 1 mm in diameter or larger in one embodiment to reduce impedance to air moving through the paths. In further embodiments, the paths may be 0.5 mm in diameter or larger. Smaller diameter paths result in an increase in impedance to the point that fans or pumps may be desirable to ensure a suitable flow of gas through the paths. However, pumps may result in increased battery drain on the mask.

Figure 3:
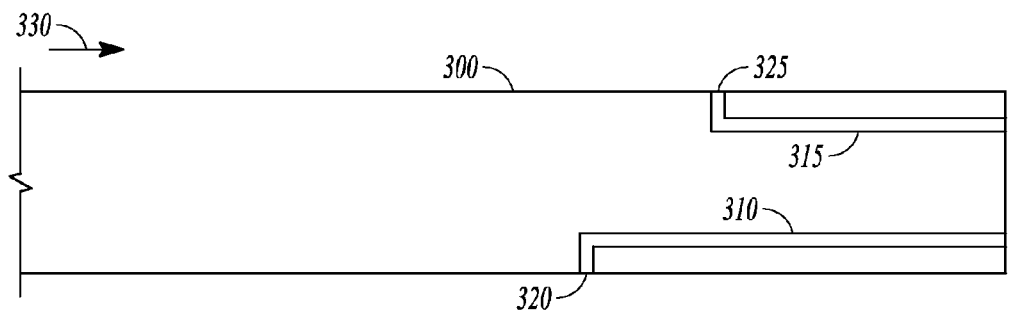
FIG. 3 is a side cross section representation of a portion of an insert according to an example embodiment.

FIG. 3 is a side cross section representation of a portion of an insert 300 having two paths 310 and 315. Path 310 has an opening 320 to the filter material. Path 315 has an opening 325 down-stream from the opening 320. Opening 320 serves as a gas sampling point, while opening 325 serves as a sample gas return point that is at a lower pressure than opening 320 when a user is breathing in. The direction of airflow within the filter material about the insert is indicated by arrow 330. In one embodiment, airflow occurs only when a user breathes in. The mask provides an alternate airflow path for air expelled by the user. In one embodiment, the openings 320 and 325 are positioned along the insert at points as close to the face 150 as possible while providing adequate differential pressure to cause the gas to flow, yet still allowing sufficient filter material from the gas return point to further filter the returned gas in a manner safe to a wearer of a respirator. In further embodiments, the positions may be determined to allow warning of filter saturation to a user sufficient to provide a desired amount of time within which to replace a saturated cartridge.

Figure 4:
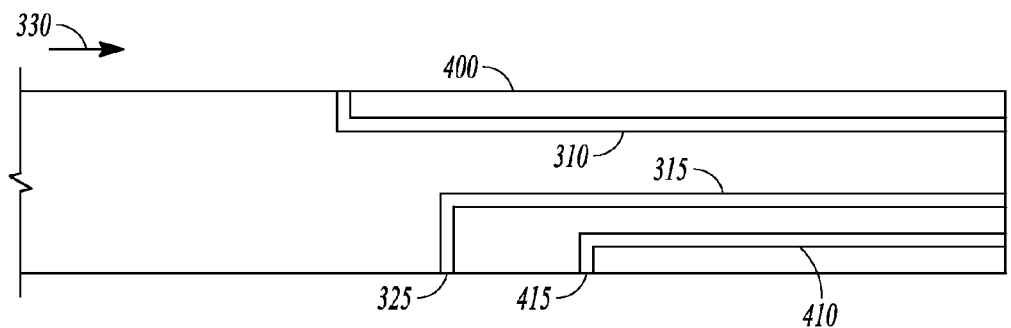
FIG. 4 is a side cross section representation of a portion of an insert according to an example embodiment.

FIG. 4 is a side cross section representation of a portion of an insert 400 having three paths according to an example embodiment. In addition to the paths illustrated in FIG. 3, path 410 is included, with a corresponding opening 415. As indicated in the description of FIG. 1, the three paths may provide alternate positions to sample and return gas from and to the filter material at different positions within the insert 400.

Figure 5:
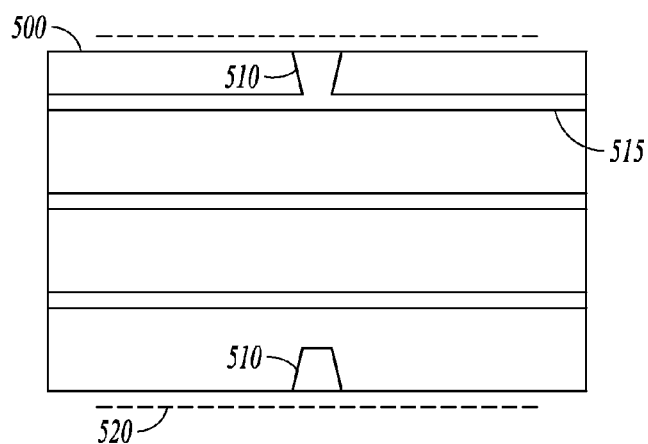
FIG. 5 is a side cross section representation of a portion of an alternative insert according to an example embodiment.

FIG. 5 is a side cross section representation of a portion of an alternative insert 500 that includes a modified sample point 510 from the filter material for one or more paths. Sample point 510 is a channel or ring that is cut into the insert to allow gas to enter the insert at any radial position of the insert. The ring 510 may also extend a desired distance from the corresponding opening without extending all the way around the insert in some embodiments. The ring 510 is cut deep and long enough to provide a larger sample point, and couple to a path indicated at 515. The ring may have parallel sides, or may have angled sides, being larger at the perimeter of the insert.

In further embodiments, the ring 510 may be cut to a desired depth at a desired longitudinal distance along the insert that does not directly connect to any path. A supplemental path may then be drilled to the desired path. In this manner, a ring may be cut at each longitudinal sample point for multiple paths, with corresponding supplemental paths to couple them to respective paths. In further embodiments, the rings may be cut a distance less than the angular distance between paths to ensure each ring connects to a single path.

In a further embodiment, a gas porous membrane 520 may be used to enclose the insert and prevent particles from entering into the paths. The membrane may encircle the entire insert, or may be positioned just over the sample points, such as rings or openings to the paths on the insert. In various embodiments, the membrane may be a filter layer such as an open structure, like a felt or nylon stocking. It may be any type of filter material screening layer or back-holding layer that allows gas to pass and inhibits filter material such as grains or dust from entering the paths.

Figure 6:
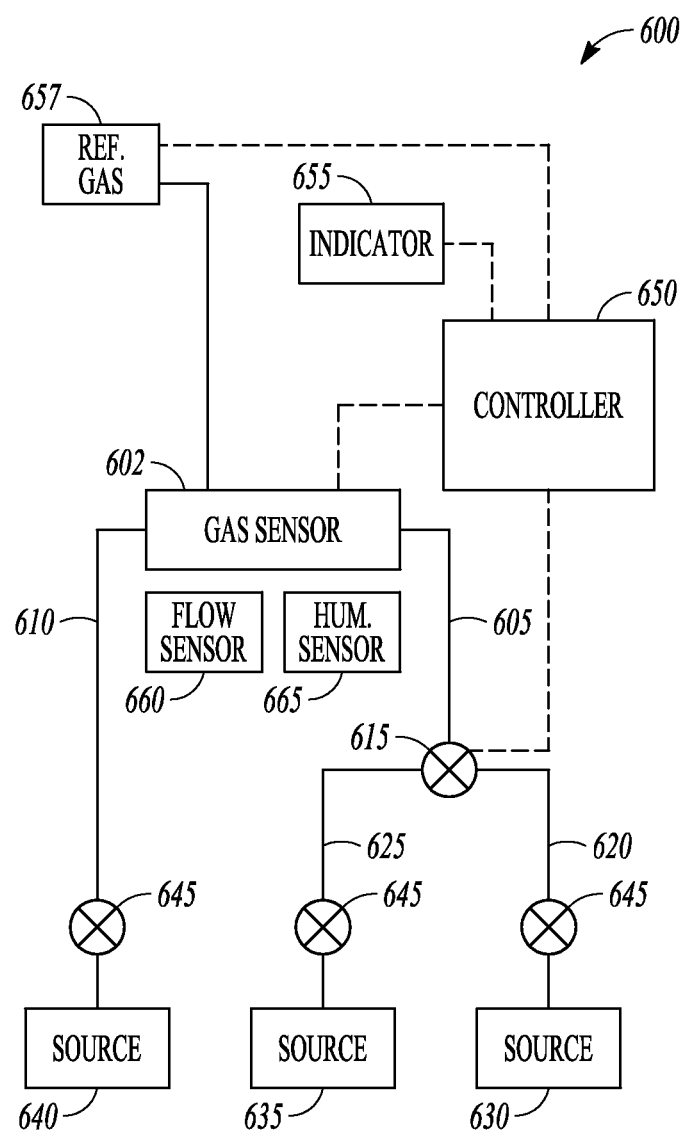
FIG. 6 is a block schematic representation of a gas sensor having multiple paths for gas according to an example embodiment.

FIG. 6 is a block schematic representation of a respirator mask 600 having a gas sensor 602 having multiple paths for handling a sample gas according to an example embodiment. Gas sensor 602 is illustrated with an input path 605 and an output path 610. In one embodiment, a valve 615 may be included in the input path 605 to select between two paths 620, 625. Each of the paths 610, 620, and 625 is coupled to a block labeled source 630, 635, and 640 respectively. Additional valves 645 may be added in each individual source path 610, 620, and 625. A controller 650 may be coupled to the gas sensor 602 and valve 615 to control them. The controller 650 may also implement algorithms to determine the saturation level of the cartridge and may also be coupled to an optical or audible indicator 655 to provide a visible or audible warning to a user of the mask 600.

In one embodiment, the sources comprises openings in a coupler that mates with face 150, such that the sources are each coupled to a corresponding insert path to either receive gas to be tested, or return the gas to the filter material. In one embodiment, the coupler is a simple flat surface having openings that are radially spaced to mate with the channels of face 150 of the cartridge. The coupler need not be flat, but is adapted to result in channels that are isolated from each other via o-rings, or the soft material of the face 150 pressing against suitable surfaces of the coupler.

In one embodiment a reference gas generator 657, such as a hydrogen generator is coupled to the gas sensor 602 to provide a reference gas to test or calibrate the sensor 602. Such source and gas generator may be included in the mask in one embodiment, as such components are reusable. In further embodiments, the source of reference gas may be included in the adapter, and may receive power from the mask or cartridge if needed. In one embodiment, the gas generator is mounted close the gas sensor to minimize the amount of gas required to reach the gas sensor. Test gas flow is occasionally switched off, and gas from the gas generator is provided to the gas sensor to determine if the sensor is still functional. The gas sensor signal may be monitored to see if the flow removes the gas effectively. The gas generator may electrochemically generate hydrogen in one embodiment, which may be detected by a metal-oxide gas sensor.

In still a further embodiment, one of the sources may include a sensor to sense whether or not the mask is being used. If it is not being used, energy savings may be realized switching off or reducing power to the gas sensor, any heaters, or circuitry of the controller 650. The gas sensor 602 itself may be operated at a low power in one embodiment to operate as a flow sensor. When flow is detected, such as that caused by a user starting to breathe, the power may be restored. Alternatively a source may represent a physical switch to turn the gas mask on or off. In still further embodiments, one of the sources may include a humidity sensor to provide humidity readings to algorithms utilized to evaluate data from the gas sensor to process gas sensor signals.

In further embodiments, one or more sensors, such as a flow sensor 660 and a humidity sensor 665 may be used to provide further information to the controller 650. Information provided by the flow sensor 660 may be used to confirm that the gas channels are not clogged, or in power management of the gas sensor. In some embodiments, heater power of the gas sensor can be switched off when there is no flow for a longer time (mask wearer has taken off mask.

While valve 615 is shown as a three way valve, it may also represent or be replaced by three two way valves, with each valve in the legs 610, 625, and 620. Other configurations may be utilized in different embodiments to obtain desired flows within the legs for receiving and returning air to the insert, and controlling supply of a test gas as desired.

Figure 7:
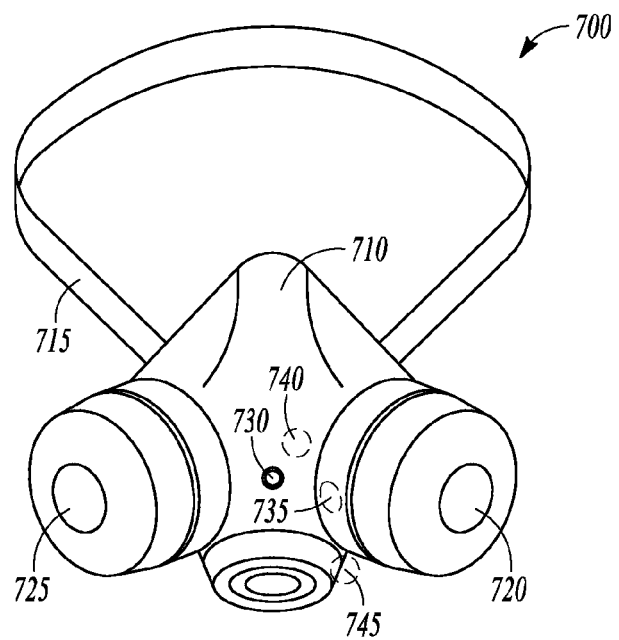
FIG. 7 is a perspective representation of a respirator having two respirator cartridges according to an example embodiment.

FIG. 7 is a perspective representation of a respirator having two respirator cartridges according to an example embodiment. The respirator 700 includes a face mask 710 having straps 715 for coupling the face mask 700 to a user face. The face mask 710 has two receptacles for two cartridges 720 and 725 to provide passages for filtered air to a wearer of the mask. Note that exhaled air may leave the mask through a one way valve, and is not returned to the cartridges.

In one embodiment, at least one receptacle has a face to mate with face 150 of a cartridge having an insert. The other receptacle need not have such a face, as it may have a cartridge without an insert attached to it. Having at least one cartridge with an insert to allow for testing of the filter material in the cartridge is sufficient, as both cartridges will have filter material being used at the about the same rate. The cartridge with the insert may in fact be sensed as becoming filled with contaminants more quickly, because if it has the same size cartridge, the cartridge without the insert may have more filter material and may be consumed more slowly. In further embodiments, both receptacles may be configured to couple to cartridges with inserts to test each cartridge independently.

In one embodiment, an optical indicator 730 may be included in the mask and controlled by a controller to indicate when the cartridges need replacing. The optical indicator 730 may be a light emitting diode (LED) or other visible indicator that is controlled by a control electronics, that also may keep track of use of the mask, and provide battery monitoring. In one embodiment, a battery may be mounted on the strap 715 behind the head of the user to balance the weight of the respirator and not make the mask heavier than it needs to be.

In one embodiment, the insert in the filter material is located near position 735 within the cartridge 720. The control electronics may be located in several different positions, such as at 740 on or within the face mask 710, or at 745 on clothing on the user. The control electronics is powered, and by placing it on something separate from the cartridges, it may be easily reused for new cartridges. It may also be removably placed on the cartridge in some embodiments, and have a self contained power supply or connection to a power supply.

Figure 8:
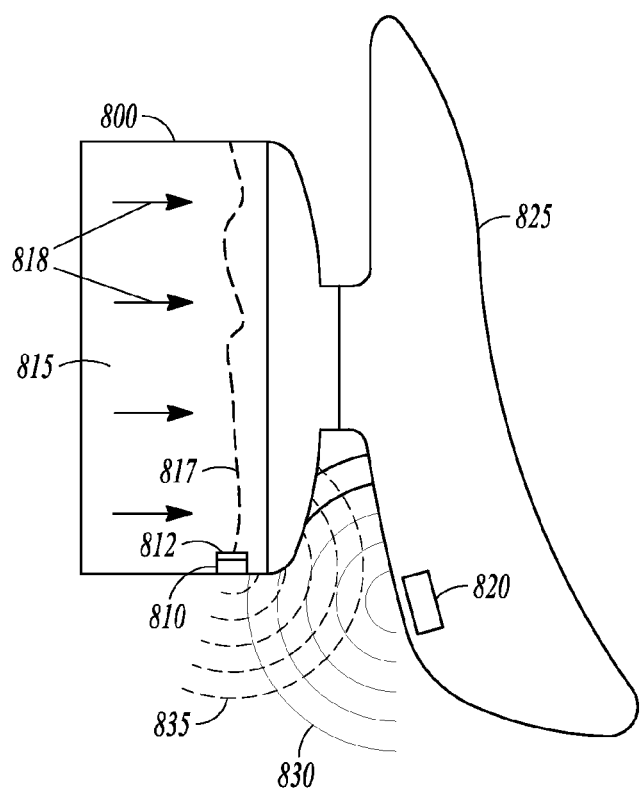
FIG. 8 is a cut away side view representation of a cartridge having remote gas sensors according to an example embodiment.

FIG. 8 is a cut away side view representation of a cartridge 800 having at least one remote gas sensitive device 810 according to an example embodiment. The remote gas sensitive device 810 is placed within or on the cartridge 800, and has gas contact with the filter material 815 at a point near the wall of the cartridge. When the cartridge fills up with target gases, the filled region will reach a point as indicated by a broken line 817 where target gases start to be detected by the remote gas sensitive device or sensor 810. In one embodiment, line 817 represents a border between a saturated and an unsaturated filter material or absorbent. Airflow in the cartridge is indicated by arrows 818.

While the remote sensor 810 is disposable, the base station 820 may be reused repeatedly for new cartridges. Because the remote sensor 810 is disposable and used only once, it may include an absorptive layer 812 that facilitates close to irreversible absorption of gas components in the air, which allows detecting better long exposures of small gas concentrations in the sample air. In one example embodiment, the remote sensor 810 is a SAW with a silver layer that absorbs hydrogen sulfide irreversibly and, above a certain dose of the gas, leads to an indication to replace the cartridge.

A base station 820 may be coupled to a face mask 825, and emits electromagnetic waves indicated by solid arcs 830, which are altered at the remote gas sensor 810 and send back as represented by broken arcs 835. These return signals are detected by the base station 820. The remote sensor 810 does not need a power supply, because the needed energy is supplied with the radiation from the base station 820. The base station 820 is separated from the remote sensor 810 by an air gap and insulating layers, but still placed close to it to keep the needed power low. The base station 820 may be mounted inside or on the respiratory mask 825, as shown, or on the clothes of the wearer of the mask. While the remote sensor 810 is disposable, the base station 820 may be reused repeatedly for new cartridges.

In various embodiments, the gas sensitive devices may be RFID (radio frequency identification) or SAW (surface acoustic wave) sensors. The shown sensor 810 is meant to represent one or more sensors that may be dispersed about the cartridge to provide one or more data points for determining saturation of the cartridge.

Figure 9:
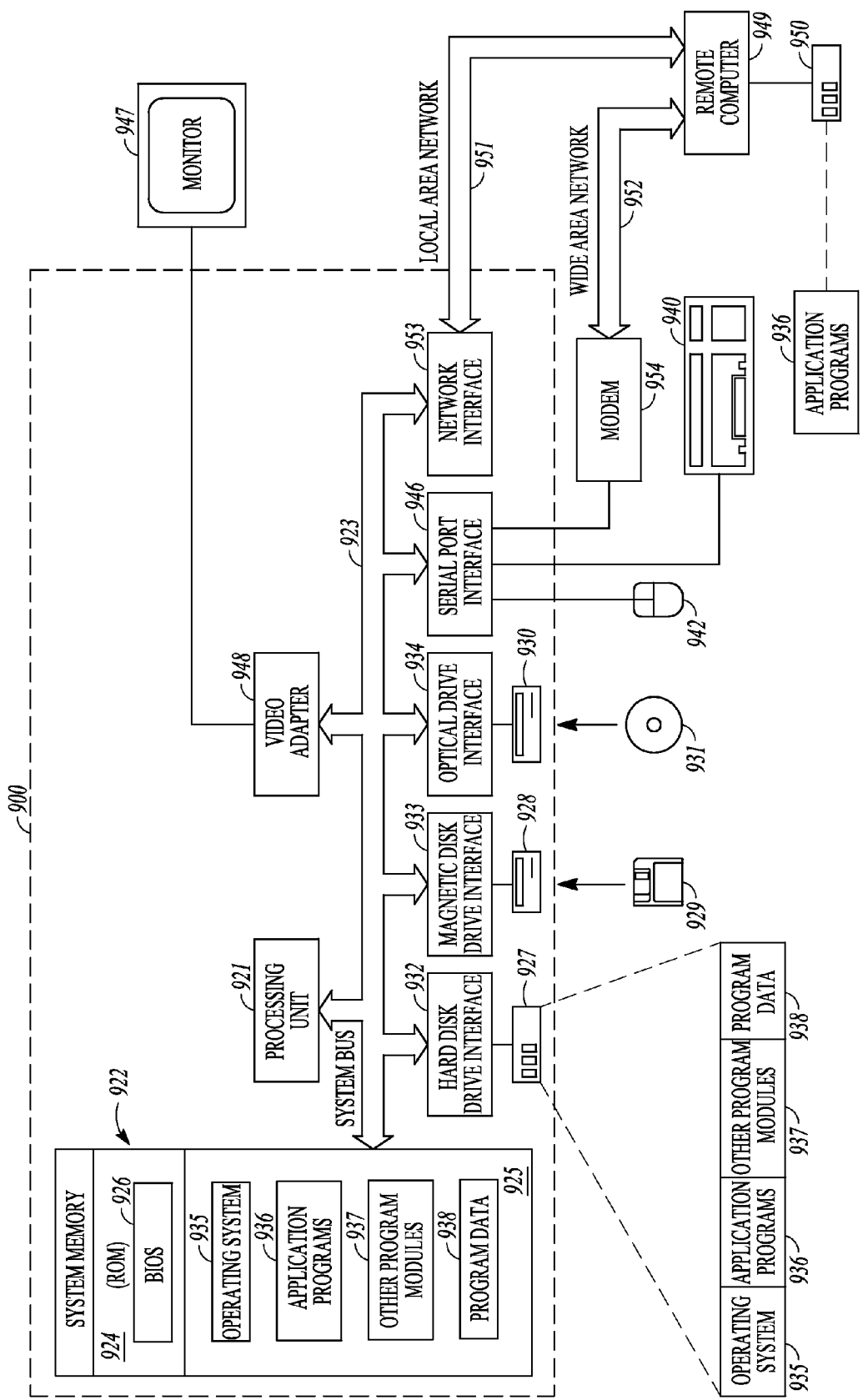
FIG. 9 is a block diagram of a computing system for controlling and calculating algorithms of various example embodiments.

FIG. 9 is a block diagram of a computing system for controlling and calculating algorithms of various example embodiments. In the embodiment shown in FIG. 9, a hardware and operating environment is provided that may be used as control circuitry. In some embodiments, many of the components may be eliminated to implement the algorithms and control functions described.

As shown in FIG. 9, one embodiment of the hardware and operating environment includes a general purpose computing device in the form of a computer 900 (e.g., a personal computer, workstation, or server), including one or more processing units 921, a system memory 922, and a system bus 923 that operatively couples various system components including the system memory 922 to the processing unit 921. There may be only one or there may be more than one processing unit 921, such that the processor of computer 900 comprises a single central-processing unit (CPU), or a plurality of processing units, commonly referred to as a multiprocessor or parallel-processor environment. In various embodiments, computer 900 is a conventional computer, a distributed computer, or any other type of computer.

The system bus 923 can be any of several types of bus structures including a memory bus or memory controller, a peripheral bus, and a local bus using any of a variety of bus architectures. The system memory can also be referred to as simply the memory, and, in some embodiments, includes read-only memory (ROM) 924 and random-access memory (RAM) 925. A basic input/output system (BIOS) program 926, containing the basic routines that help to transfer information between elements within the computer 900, such as during start-up, may be stored in ROM 924. The computer 900 further includes a hard disk drive 927 for reading from and writing to a hard disk, not shown, a magnetic disk drive 928 for reading from or writing to a removable magnetic disk 929, and an optical disk drive 930 for reading from or writing to a removable optical disk 931 such as a CD ROM or other optical media.

The hard disk drive 927, magnetic disk drive 928, and optical disk drive 930 couple with a hard disk drive interface 932, a magnetic disk drive interface 933, and an optical disk drive interface 934, respectively. The drives and their associated computer-readable media provide non volatile storage of computer-readable instructions, data structures, program modules and other data for the computer 900. It should be appreciated by those skilled in the art that any type of computer-readable media which can store data that is accessible by a computer, such as magnetic cassettes, flash memory cards, digital video disks, Bernoulli cartridges, random access memories (RAMs), read only memories (ROMs), redundant arrays of independent disks (e.g., RAID storage devices) and the like, can be used in the exemplary operating environment.

A plurality of program modules can be stored on the hard disk, magnetic disk 929, optical disk 931, ROM 924, or RAM 925, including an operating system 935, one or more application programs 936, other program modules 937, and program data 938. Programming for implementing one or more processes or method described herein may be resident on any one or number of these computer-readable media.

A user may enter commands and information into computer 900 through input devices such as a keyboard 940 and pointing device 942. Other input devices (not shown) can include a microphone, joystick, game pad, satellite dish, scanner, or the like. These other input devices are often connected to the processing unit 921 through a serial port interface 946 that is coupled to the system bus 923, but can be connected by other interfaces, such as a parallel port, game port, or a universal serial bus (USB). A monitor 947 or other type of display device can also be connected to the system bus 923 via an interface, such as a video adapter 948. The monitor 947 can display a graphical user interface for the user. In addition to the monitor 947, computers typically include other peripheral output devices (not shown), such as speakers and printers.

The computer 900 may operate in a networked environment using logical connections to one or more remote computers or servers, such as remote computer 949. These logical connections are achieved by a communication device coupled to or a part of the computer 900; the invention is not limited to a particular type of communications device. The remote computer 949 can be another computer, a server, a router, a network PC, a client, a peer device or other common network node, and typically includes many or all of the elements described above I/O relative to the computer 900, although only a memory storage device 950 has been illustrated. The logical connections depicted in FIG. 9 include a local area network (LAN) 951 and/or a wide area network (WAN) 952. Such networking environments are commonplace in office networks, enterprise-wide computer networks, intranets and the internet, which are all types of networks.

When used in a LAN-networking environment, the computer 900 is connected to the LAN 951 through a network interface or adapter 953, which is one type of communications device. In some embodiments, when used in a WAN-networking environment, the computer 900 typically includes a modem 954 (another type of communications device) or any other type of communications device, e.g., a wireless transceiver, for establishing communications over the wide-area network 952, such as the internet. The modem 954, which may be internal or external, is connected to the system bus 923 via the serial port interface 946. In a networked environment, program modules depicted relative to the computer 900 can be stored in the remote memory storage device 950 of remote computer, or server 949. It is appreciated that the network connections shown are exemplary and other means of, and communications devices for, establishing a communications link between the computers may be used including hybrid fiber-coax connections, T1-T3 lines, DSL's, OC-3 and/or OC-12, TCP/IP, microwave, wireless application protocol, and any other electronic media through any suitable switches, routers, outlets and power lines, as the same are known and understood by one of ordinary skill in the art.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A device comprising:
a cartridge containing a filter material, wherein the cartridge includes an adapter operable to removably couple to a respirator mask; and
an insert extending from the adapter upstream in the cartridge through at least a portion of the filter material and having a first path with an opening to provide a sample of air that is representative of the saturation of the filter material;
wherein the first path extends from the adapter upstream in the cartridge.

2. The device of claim 1 wherein the insert includes a second path and opening to return the sample of air to the filter material, wherein the second path extends from the adapter upstream in the cartridge.

3. The device of claim 2 wherein the second path opening is downstream of the path opening of the first path to provide a difference in pressure between the openings when air is drawn through the filter material by a user of the device.

4. The device of claim 1 wherein the adapter provides the sample of air to a gas sensor, and wherein the gas sensor is incorporated into the respirator mask.

5. The device of claim 4 wherein the adapter comprise at least two circular channels, each of which is coupled to a respective path to provide rotational symmetry to couple to the gas sensor.

6. The device of claim 1 and further comprising a remotely readable RFID or SAW sensor supported by the cartridge.

7. The device of claim 6 wherein at least one of the remotely readable sensors is placed inside the cartridge.

8. The device of claim 7 where an absorption layer on the remote sensor facilitates irreversible absorption or close to irreversible absorption of gas components in the sample air.

9. The device of claim 1 and further comprising a gas permeable filter layer positioned between the channel opening and the filter matrial.

10. A device comprising:
a cartridge containing a filter material and an adapter operable to couple to a gas sensor incorporated into a. respirator mask; and
an insert extending from the adapter upstream in the cartridge through at least a portion of the filter material and having a first path with an opening to provide a sample of air to the gas sensor that is representative of the saturation of the filter material and a second path and opening to return the sample of air to the filter material, the second path opening being downstream of the path opening of the first path to provide a difference in pressure between the openings when air is drawn through the filter material by a user of the device;
wherein the first path extends from the adapter upstream in the cartridge, and the second path extends from adapter upstream in the cartridge.

11. The device of claim 10 wherein the adapter comprises at least two circular channels, each of Which is coupled to a respective path to provide rotational symmetry to couple to the gas sensor.

12. The device of claim 10 further comprising a gas permeable filter layer positioned between the channel opening and the filter material.

13. The device of claim 10 further comprising a remotely readable RFID or SAW sensor supported by the cartridge.

14. The device of claim 13 wherein at least one of the remotely readable sensors is placed inside the cartridge.

15. The device of claim 14 wherein an absorption layer on the remote sensor facilitates irreversible absorption or close to irreversible absorption of gas components in the sample air.

16. A device comprising:
a cartridge containing a filter material and an adapter operable to couple to a gas sensor incorporated into a respirator mask, the adapter comprising at least two circular channels, each of which is coupled to a respective path to provide rotational symmetry to couple to the gas sensor;
an insert extending from the adapter upstream in the cartridge through at least a portion of the filter material and having a first path with an opening to provide a sample of air to the gas sensor that is representative of the saturation of the filter material, and a second path and opening to return the sample of air to the filter material, the second path opening being downstream of the path opening of the first path to provide a difference in pressure between the openings when air is drawn through the filter material by a user of the device; and a remotely readable RFID or SAW sensor supported by the cartridge.

17. The device of claim 16 further comprising a gas permeable filter layer positioned between the channel opening and the filter material.

18. The device of claim 16 wherein at least one of the remotely readable sensors is placed inside the cartridge.

19. The device of claim 18 wherein an absorption layer on the remote sensor facilitates irreversible absorption or dose to irreversible absorption of gas components in the sample air.

* * * * *